United States Patent [19]
Bayonnet

[11] 3,952,194
[45] Apr. 20, 1976

[54] DEVICE FOR IDENTIFYING THE LOCATION OF DEFECTS IN A TIRE BEING X-RAYED

[75] Inventor: Jack L. Bayonnet, Akron, Ohio
[73] Assignee: The Goodyear Tire & Rubber Company, Akron, Ohio
[22] Filed: Nov. 11, 1974
[21] Appl. No.: 522,409

[52] U.S. Cl. .............................. 250/358 T; 250/476
[51] Int. Cl.² ......................................... G01N 23/00
[58] Field of Search ................ 250/358 T, 360, 476

[56] References Cited
UNITED STATES PATENTS
3,789,226  1/1974  Green et al. ..................... 250/358 T
3,848,136  11/1974  Seldin ................................. 250/476

*Primary Examiner*—Davis L. Willis
*Attorney, Agent, or Firm*—F. W. Brunner; H. E. Hummer

[57] ABSTRACT

An elastic band for positioning around the outer periphery of a tire being X-rayed and inspected for defects. A set of Arabic numerals are spaced equally around the band for identifying the location of a defect in the tire when it appears on a television monitor used in conjunction with the system of X-raying the tire.

17 Claims, 2 Drawing Figures

DEVICE FOR IDENTIFYING THE LOCATION OF DEFECTS IN A TIRE BEING X-RAYED

BACKGROUND OF THE INVENTION

The invention is particularly well suited for use in the inspection of wire reinforced tires by X-raying them, for example, in accordance with any of the systems or apparatuses described in U.S. Pat. Nos. 3,621,246; 3,621,247; 3,761,722, and 3,789,226. Such systems essentially comprise rotating a tire, to be inspected, about its center axis. An X-ray tube is positioned for emitting X-rays through the rotating tire from the inner peripheral surface thereof. The X-rays are received on an input screen of an image amplifier tube which is positioned outside the tire in alignment with the port through which the rays emit from the X-ray tube. A television camera, affiliated with the output screen of the image amplifier tube, is used to communicate visual information of the internal construction of the tire to a television monitor which is located in a room remote from where the tire is being X-rayed. The density of the televised achromatic images of the internal construction of the tire appearing on the TV monitor, can be varied by conventional adjustments for lightening and darkening the images or pictures. Moreover, the images can be enlarged on the TV monitor to view smaller details of the tire construction, if necessary.

The system of inspecting tires by X-raying them has proven beneficial in locating defects not readily discernible by other methods. However, it is difficult pinpointing the actual location of a defect when it is observed on the TV monitor. The invention is directed to a mechanical indicator for visually showing an operator, watching the TV monitor, just where the defect is on the tire. The invention is especially useful in checking tires to determine if they are built according to specification. The specification to which a tire is built indicates the arcuate positions where the different splices of the various components should be made around the tire. The tire is conveniently sectionalized like a clock so that a particular splice can be specified as being, for example, at the 12, 2, or 6 o'clock position. A tire builder's number is normally molded in the outer sidewall of the tire adjacent the tread splice which is considered to be at the 12 o'clock position. It can be appreciated that using the system of X-raying a tire, the various locations of the different splices can be easily checked on the television monitor, if the various sectors of the clock are also readily discernible. The invention accomplishes this.

Briefly stated, the invention is in a device for identifying the location of a defect in a tire being X-rayed. The device comprises a continuous band which is positioned around the tire. The band has a thickness and density for producing on a television monitor, an achromatic image which does not interfere with the observance of images of important components of the tire desired to be inspected. A predetermined set of indicia, such as Arabic numerals, are spaced equally around the band. The numerals each have a thickness and density for producing on the television monitor, an achromatic image which visually contrasts with the corresponding images produced by the components of the tire desired to be viewed, such that the indicia are readily discernible on the TV monitor. Thus, any defect discovered in the tire can be quickly related to indicia also visible on the TV monitor.

DESCRIPTION OF THE DRAWING

The following description of the drawing will be better understood by having reference to the annexed drawing, wherein.

DESCRIPTION OF THE INVENTION

Figure 1:
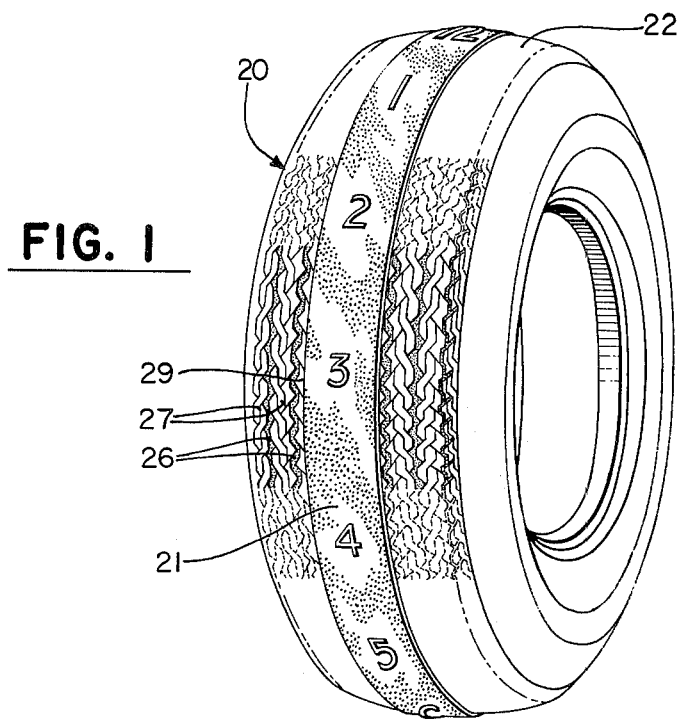
FIG. 1 is a perspective view of a tire having positioned thereon, an indicator band made in accordance with the invention.

Referring more particularly to FIG. 1, there is shown a wire-belted, radial tire 20 which is mounted for rotation about its center axis, i.e. on any of the apparatuses shown and described in the aforementioned patents. An indicator, or band 21 is positioned centrally around the outer periphery, or tread 22 of the tire 20. The band 21, in this instance, is composed of any suitable elastic material which can be stretched to accommodate positioning the band 21 around conventionally sized tires, e.g. tires with 13, 14, and 15-inch bead diameters. Anyone experienced in viewing a television monitor during the X-raying and inspection of a tire, realizes that an image created by the elastic band 21 could visually obliterate more important images of the components of the tire. The lightness or darkness of an image depends on the thickness and density of the object casting the image. Thus, it is important that the thickness and density of the elastic band 21 be such that its achromatic image on the TV monitor, at most, blend with the lightest image produced on the TV monitor. As a practical matter, the lightest images are those of the rubbery material of the tire, especially the thinnest section of rubbery material taken at the grooves in the tread pattern. Therefore, the thickness and density of the elastic band 21 should be such that the image it casts on the TV monitor should not be any darker than the image cast by the rubbery material in the groove areas of the tread of the tire.

Figure 2:
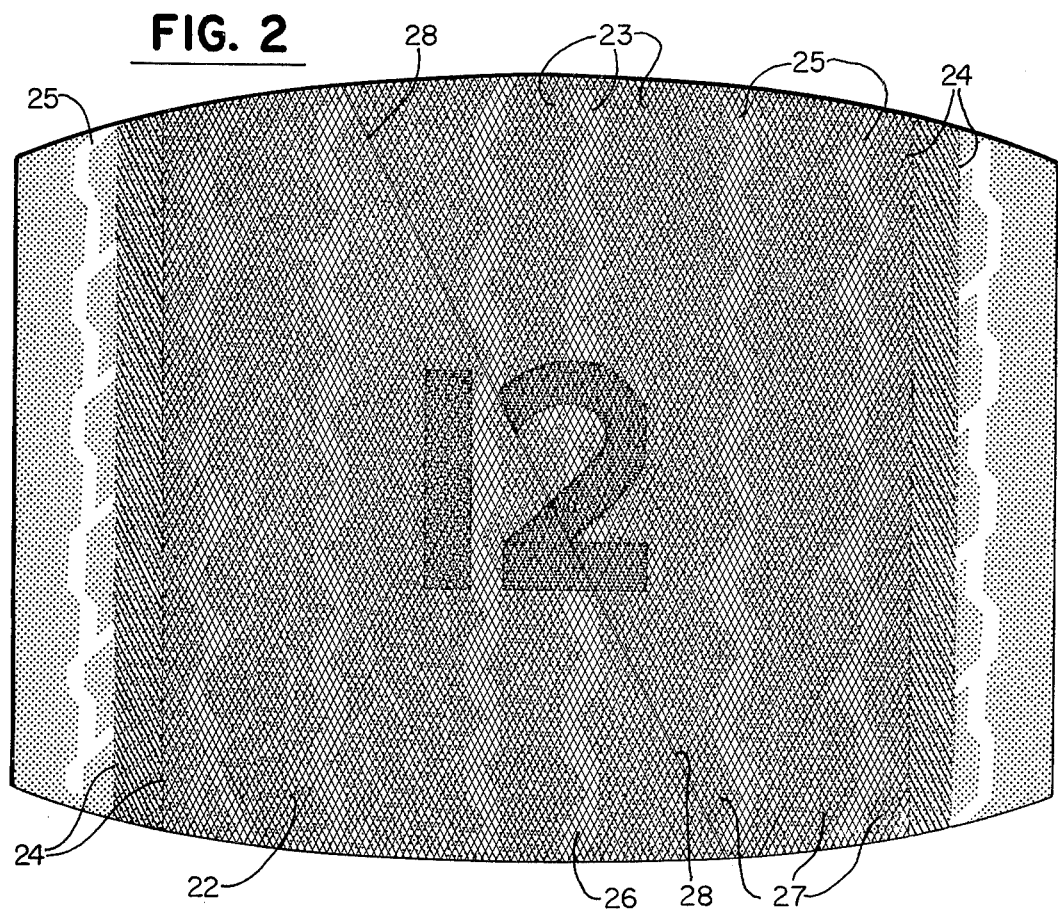
FIG. 2 is an image appearing on the television monitor, as viewed by an operator inspecting the tire.

A predetermined set of indicia are spaced equally around the elastic band 21. For example, Arabic numerals 1–12, are equally spaced on the elastic band 21 to simulate the face, or sectors of a clock. The numerals 1–12 have a thickness and density which, unlike the elastic band 21, are designated for producing on the TV monitor, an achromatic image which visually contrasts with the lightest and darkest images produced by the rubbery material of the tire, e.g. images cast by the pattern of grooves and ribs in the tread. Numerals composed of aluminum, having a thickness of about ⅛ inches, produced a good contrasting image without completely obscuring images of other components of the tire 20. For example, as seen in FIG. 2, the images of the wire reinforcement cords 23 of the belt structure 24 are darker than the images of the rubbery material and numeral 12 and, therefore, are not obscured by the numerals. It was found that an article composed of brass having a thickness of about 1/16 inches, provided a very dark image which completely obscured the wire cords 23 of the belt structure 24. It was also found that rubbery material could be used for the numerals 1–12, but a thickness of about ½ inches was necessary to provide a good contrasting image for viewing tires with wire reinforced belt structures. However, a ¼ inch thickness of rubbery material was found adequate when viewing tires reinforced with textile cords. Thus, almost any material could be used for the numerals 1–12, providing it produces the desired contrast and the numerals do not become too cumbersome and impractical for securing to the elastic band 21. The width of the elastic band 21 is dependent on the width of the tread of the tire being inspected. A band width of from 2 to 4 inches is sufficient for use with most passenger tires. Wider bands are more desirable for racing tires having exceptionally wide treads, since the televised images are restricted in size. In such cases, it would be wise using several identical numbers spaced transversely across, for example, a 9-12 inch wide band with two parallel annular lines for dividing the tire tread into three annular segments, each of which segments has its own clock sections, or numerals 1–12.

A typical image appearing on the TV monitor of a radial tire with a wire reinforced belt structure, is shown in FIG. 2. The pattern of light areas 25, shown in the center portion of the image, define the grooves 26 and ribs 27 of the tread pattern which is readily discernible. The darker crisscrossing lines are the metal cords 23 of the belt structure 24. A splice 28 in the belt structure 24 is shown crossing the image in the sector of numeral 12. Assuming for the moment that this particular splice 28 is at the builder's number and not the tread splice, as previously indicated, the elastic band 21 would be positioned around the tire 20 such that the twelve o'clock position, represented by the numeral 12, is adjacent the splice 28. The other splices could then be easily checked in relation to their arcuate position by noting the different numerals appearing with the various splices. In this way, the consistency of building tires in accordance with a particular specification can be checked and action taken to improve the quality, or consistency of making the splices should they be found to vary from their specified orientations around the tire. One of the continuous, longitudinal edges 29 of the elastic band 21 is preferably provided with some type of a distinguishing mark, such as a different colored edging to help an operator properly position the band 21 on a tire being inspected.

The elastic band 21 is the simplest mechanical indicator which can be used in conjunction with drive mechanisms designed to engage the beads and rotate the tire. Such drive mechanisms are described in the aforementioned patents which also describe tire rotating mechanisms that emply rollers for engaging the outer peripheral surfaces of the tread of the tire. These drive rollers exert compressive forces against the tire sufficient to cause considerable deflection of the tread of the tire. The use of a wide elastic band 21 with raised, metal numerals 1–12, in conjunction with such drive mechanisms, is impractical since the wide band and numerals interfere with the operation of the drive rollers. It is better to use either a narrow, flexible metal band, or a small elastic string for spacing very thin, metallic numerals 1–12 which should also be flexible to conform to the deflected configuration of the tread when contacted by the drive rollers. Another solution to this particular problem would be the provision of a set of numerals 1–12 along the inner periphery, or crown of the tire. An inflatable ring, expansible with the tire, if mounted and inflated, would provide a suitable band for carrying the numerals 1–12, so long as the band is not too big and interferes with the X-ray tube positioned within the cavity of the tire.

Another simple device for correlating defects and building details of the tire to their arcuate positions around the tire in relation either to each other, or a fixed detail, or marking on the tire, envisions the use of a digital counter, adjacent the TV monitor, for visually showing the arcuate location on the tire of the image being viewed on the TV monitor. The operation of the counter is advantageously correlated to the rotation of the tire and triggered by a scanning device upon location of a fixed detail, or marking on the tire, such as a piece of magnetic tape secured to a sidewall of the tire at the tire builder's number, i.e. the 12:00 o'clock position. Thus, an operator viewing images on the TV monitor, could tell immediately the location of a defect, or building detail by noting the numeral appearing on the face of the digital counter. This particular system would not interfere with the operation of drive rollers designed to engage the outer peripheral surface of the tread of the tire.

Thus, there has been provided a simple mechanical indicator for positioning on a tire to locate the arcuate position of defects on a tire, or to check the splices of the various components to determine if they are in accordance with the specification to which the tire should be built. The tires can be inspected when they are unmolded and unvulcanized, or when they are molded and vulcanized, since the invention is designed to accommodate both types of tires.

What is claimed is:

1. A device for identifying the location of a defect, or particular building detail in a tire being rotated and X-rayed, comprising:
   a. a band positionable around the rotational axis of the tire adjacent the tread of the tire, the band having a thickness and density for producing on a television monitor, an achromatic image which will not interfere with the visual inspection of images produced on the monitor by components of the tire desired to be inspected; and
   b. a predetermined set of indicia spaced equally around the band, the indicia having a thickness and density for producing on a television monitor an achromatic image which visually contrasts with the images correspondingly produced on the monitor by components of the tire desired to be inspected.

2. The device of claim 1, wherein the band is centrally disposed around the outer periphery of the tread of the tire.

3. The device of claim 2, wherein the band is continuous and composed of elastic material.

4. The device of claim 3, wherein the band is composed of rubbery material.

5. The device of claim 1, wherein the indicia are composed of metal having a thickness and density for producing on the TV monitor, an image which does not obscure correspondingly formed images of wire reinforcement cords of the tire.

6. The device of claim 1, wherein the set of indicia include Arabic numerals 1 through 12 and any fractions thereof.

7. A method of visually inspecting a tire and correlating observable defects, or building details of the tire, to arcuate positions on the tire, comprising:
   a. rotating a tire to be inspected;
   b. passing X-rays through the tire from the inner peripheral surfaces thereof;
   c. translating X-rays passed through the tire into images observable on a television monitor;
   d. correlating the images to indicia representing arcuate positions around the tire; and e. providing a visual display of the indicia in conjunction with the images.

8. The method of claim 7, wherein the indicia are numerals 1 through 12 12 any fractions thereof.

9. The method of claim 8, wherein the numeral 12 is always in reference to a fixed detail of the tire.

10. The method of claim 8, which includes positioning a continuous band around the tire, prior to passing the X-rays therethrough, the band having the numerals equally spaced therearound.

11. The method of claim 10, wherein the band is elastic.

12. The method of claim 8, wherein the numerals have a thickness and density sufficient to produce on the TV monitor, images which are achromatically in contrast with images produced by the tire.

13. The method of claim 7, including the inspection of a tire which is unmolded and unvulcanized.

14. The method of claim 7, including the inspection of a tire which is molded and vulcanized.

15. The method of claim 7, including checking the arcuate positions of the splices of different components of the tire to determine if the splices are in conformance with a specification to which the tire should be built.

16. The method of claim 7, wherein a digital counter is used for displaying indicia correlated to a specific detail of the tire.

17. The method of claim 16, wherein the indicia include numerals 1 through 12 and any fractions thereof.

* * * * *